United States Patent
Nishii et al.

(10) Patent No.: US 9,468,388 B2
(45) Date of Patent: Oct. 18, 2016

(54) ELECTROCARDIOGRAPHIC WAVEFORM MEASURING APPARATUS

(71) Applicant: DENSO CORPORATION, Kariya, Aichi-pref. (JP)

(72) Inventors: Katsuyoshi Nishii, Okazaki (JP); Kazuhiro Sakai, Gifu (JP)

(73) Assignee: DENSO CORPORATION, Kariya (JP)

( * ) Notice: Subject to any disclaimer, the term of this patent is extended or adjusted under 35 U.S.C. 154(b) by 170 days.

(21) Appl. No.: 14/242,346

(22) Filed: Apr. 1, 2014

(65) Prior Publication Data

US 2014/0323838 A1 Oct. 30, 2014

(30) Foreign Application Priority Data

Apr. 25, 2013 (JP) .................................. 2013-92721
Apr. 25, 2013 (JP) .................................. 2013-92722

(51) Int. Cl.
- *A61B 5/0408* (2006.01)
- *A61B 5/00* (2006.01)
- *A61B 5/0428* (2006.01)

(52) U.S. Cl.
CPC ........... *A61B 5/0408* (2013.01); *A61B 5/0428* (2013.01); *A61B 5/04085* (2013.01); *A61B 5/6891* (2013.01); *A61B 5/6893* (2013.01); *A61B 5/7203* (2013.01)

(58) Field of Classification Search
CPC ............ A61B 5/04085; A61B 5/0408; A61B 5/6893
See application file for complete search history.

(56) References Cited

U.S. PATENT DOCUMENTS

2015/0133804 A1* 5/2015 Sugiyama ............ A61B 5/0408
600/509

FOREIGN PATENT DOCUMENTS

| JP | 2007-142576 A | 6/2007 |
|---|---|---|
| JP | 2009-050679 A | 3/2009 |
| JP | 2011-024903 A | 2/2011 |
| JP | 2012-161490 A | 8/2012 |
| JP | 2013-063214 A | 4/2013 |

OTHER PUBLICATIONS

Office Action mailed Mar. 23, 2015 issued in corresponding JP patent application No. 2013-092721 (and English translation).

* cited by examiner

*Primary Examiner* — Lee S Cohen
(74) *Attorney, Agent, or Firm* — Posz Law Group, PLC

(57) ABSTRACT

An electrocardiographic waveform measuring apparatus mounted in a seat with a seat skin element includes: a sensor electrode at a seat interior side of the seat to be covered with the seat skin element; an insulating elastic element at the seat interior side of the sensor electrode in the seat opposite to the seat skin element to face the sensor electrode; a guard electrode at the seat interior side of the insulating elastic element in the seat opposite to the sensor electrode to be opposed to the sensor electrode through the insulating elastic element; and a housing case at the seat interior side of the insulating elastic element in the seat opposite to the sensor electrode to be opposite to the insulating elastic element. The housing case accommodates a sensor circuit with an amplifier circuit, to which a potential signal of the sensor electrode is initially input.

7 Claims, 13 Drawing Sheets

TEST A1

TEST A2

TEST A3

TEST A4

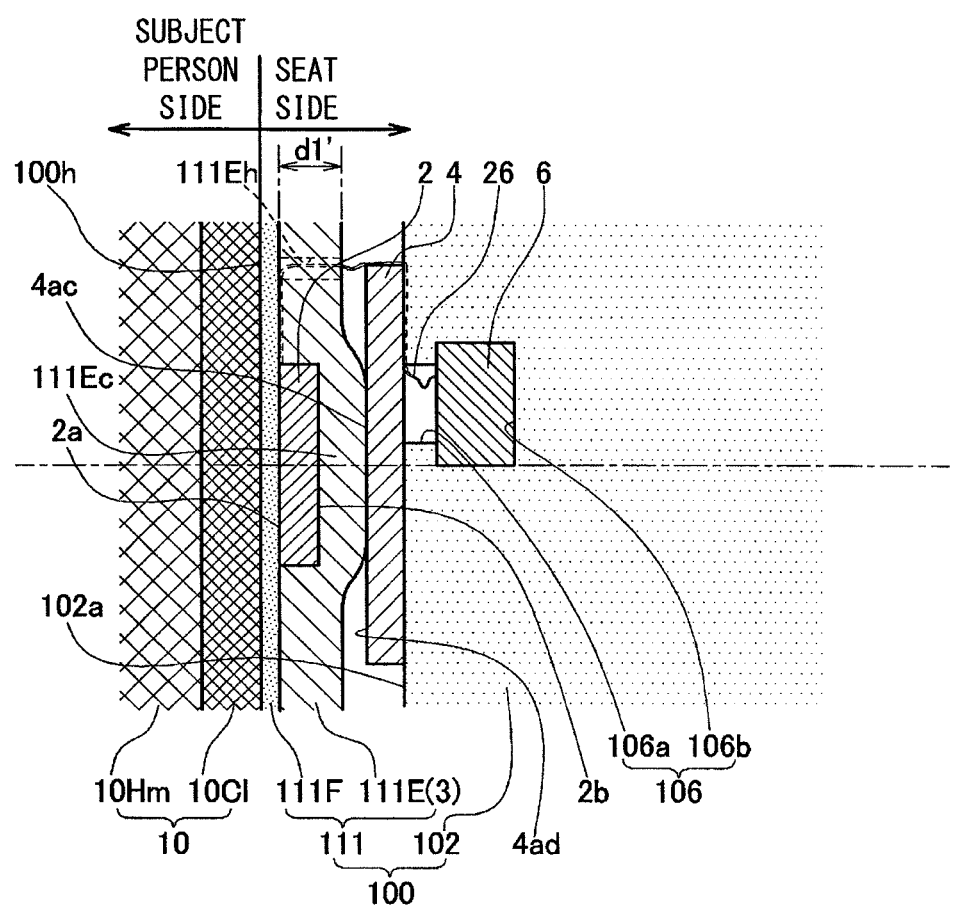

ELECTROCARDIOGRAPHIC WAVEFORM MEASURING APPARATUS

CROSS REFERENCE TO RELATED APPLICATIONS

This application is based on Japanese Patent Applications No. 2013-92721 filed on Apr. 25, 2013, and No. 2013-92722 filed on Apr. 25, 2013, the disclosures of which are incorporated herein by reference.

TECHNICAL FIELD

The present disclosure relates to an electrocardiographic waveform measuring apparatus, which measures an electrocardiographic waveform of a user who comes into contact therewith.

BACKGROUND

For example, as disclosed in JP-A-2012-161490, an electrocardiographic (i.e., ECG) waveform measuring apparatus, provided in a seat of a vehicle or the like, which measures an electrocardiographic waveform of a user who sits thereon includes an electrode potential detection unit having paired sensor electrodes which are disposed in a backrest portion of a seat so as to interpose a predetermined heart position therebetween at which the heart of a user who sits on the seat is located and to be parallel to a backrest surface of the seat, a guard electrode which is disposed at the outer circumferential side of each sensor electrode or the seat interior side so as not to influence a high impedance input to the sensor electrodes, and an insulating material which is disposed between these sensor electrodes and the guard electrode.

Each of the paired sensor electrode is connected to the input terminal of a sensor circuit including a known operational amplifier. Each of both the sensor circuits outputs a potential of the sensor electrode to be connected, as a detection signal, from the output terminal thereof. The detection signals which are output from both the sensor circuits are input to the input terminal of a differential amplifier, and a differential signal obtained by taking a difference between these detection signals is output from the output terminal thereof. The output differential signal is input to a band-pass filter, and is changed to an analog signal obtained by passing through a component of an electrocardiographic signal band (for example, 0.2 Hz to 35 Hz). Further, the analog signal is input to an AD converter and is converted into a digital signal. This digital signal is an electrocardiographic signal of the user who sits on the seat, and an electrocardiographic waveform obtained from the electrocardiographic signal is used in a variety of control of a vehicle in this case.

On the other hand, a circuit substrate having the sensor circuit formed thereon is housed in a hard housing case, and is disposed at a position relatively close to the corresponding sensor electrode which is located inside the backrest portion of the seat.

In the past, the electrode potential detection unit including the sensor electrode, the insulating material, and the guard electrode has been disposed slightly inside from the backrest surface of the seat. However, for the purpose of an improvement in detection sensitivity, there is a desire for disposing the electrode potential detection unit at a position closer to the backrest surface of the seat. However, the approximation of the electrode potential detection unit to the backrest surface of the seat leads to the approximation of a housing case that houses a sensor circuit substrate to the backrest surface of the seat. As a result, a problem is brought about in that sitting discomfort such as the seated user's feeling of a hard housing case on his/her back is caused.

Further, the seat of a vehicle or the like is configured such that a seat body covering material that forms a contact surface with a user who sits thereon is formed so as to cover the surface of a seat body material which is separate from the seat body covering material, but the sensor electrode is disposed relatively inside from the seat.

On the other hand, for the purpose of an improvement in detection sensitivity, there is a desire for the sensor electrode being closer to the backrest surface of the seat. However, the seat body covering material is a covered body covered with the seat body material, and position displacement between the seat body material and the covered body, position displacement between the clothes of a user or the like and the covered body, and the like occur. For this reason, there is the possibility of static charge being accumulated inside the covered body due to friction at that time. Static charge accumulated inside the covered body is locally discharged to an exposed surface (electrode surface) of the sensor electrode at the moment when relative position movement or pressure such as traveling vibration or pressure of the seat body covering material caused by a user who sits on the seat is generated between the seat body covering material and the sensor electrode, and is superimposed on an electrocardiographic signal as electric noise, which leads to the possibility of a deterioration in detection accuracy being caused.

SUMMARY

It is an object of the present disclosure to provide an electrocardiographic waveform measuring apparatus in which, even when a sensor electrode is disposed at a position closer to the backrest surface of the seat, a user is not made to feel a sitting discomfort of the seat, and a high denoising effect is realized simultaneously.

Further, it is another object of the present disclosure to provide an electrocardiographic waveform measuring apparatus which is not likely to be influenced by electric noise due to the seat body covering element that covers the sensor electrode when the sensor electrode is disposed on the seat body element in an exposed state.

According to a first aspect of the present disclosure, an electrocardiographic waveform measuring apparatus mounted in a seat with a seat skin element, which provides a contact surface with a user, the electrocardiographic waveform measuring apparatus includes: a sensor electrode disposed at a seat interior side of the seat as a back side of the contact surface so that the sensor electrode is covered with the seat skin element; an insulating elastic element disposed at the seat interior side of the sensor electrode in the seat opposite to the seat skin element so that the insulating elastic element faces the sensor electrode, and the insulating elastic element has a thickness larger than the seat skin element; a guard electrode disposed at the seat interior side of the insulating elastic element in the seat opposite to the sensor electrode so that the guard electrode is opposed to the sensor electrode through the insulating elastic element; and a housing case disposed at the seat interior side of the insulating elastic element in the seat opposite to the sensor electrode so that the housing case is opposite to the insulating elastic element, the housing case accommodating a sensor circuit with at least an amplifier circuit, to which a potential signal indicating a potential of the sensor electrode is initially input.

In the above apparatus, both effects of an improvement in a sitting discomfort such as a feeling of a sense of contact with the hard housing case and a reduction in noise can be obtained by causing the hard housing case to be located at the rear (seat interior side) of the insulating elastic element thicker than the seat skin element that forms an outermost surface of the seat.

In the above apparatus, an inside elastic element which is separate from the insulating elastic element disposed between the sensor electrode and the guard electrode may be disposed on the rear surface of the seat skin element that forms the outermost surface of the seat, and the sensor electrode (2) may be disposed on the rear thereof. In this case, the above sitting discomfort can be further improved by the presence of the inside elastic element. However, in spite of the inside elastic element being capable of further improving the aforementioned sitting discomfort as the thickness thereof is made larger, a new problem occurs which results in an increase in noise due to an increase in the amount of inclusions between a human body and the seat. On the other hand, an increase in noise can be suppressed by increasing the thickness of the insulating elastic element.

According to a second aspect of the present disclosure, an electrocardiographic waveform measuring apparatus includes: a sensor electrode disposed between a seat body covering element and a seat body element in a seat. The seat body covering element covers a surface of the seat body element, which is different from the seat body covering element. The seat body covering element provides a contact surface with a user. The sensor electrode includes a first sensor electrode having a first electrode surface and a second sensor electrode having a second electrode surface. The first sensor electrode is installed to the seat body element so that the first electrode surface is exposed to a seat body covering material side. The second sensor electrode is installed to the seat body covering material element. The second electrode surface slidably contacts with the first electrode surface.

According to the above apparatus, since static charge accumulated in the seat body covering element is immediately diffused into the electrode surface of the second sensor electrode on the seat body covering element side, local discharge does not occur. In addition, since the second sensor electrode and the first sensor electrode are always in surface contact with each other, the detection of a potential signal for obtaining an electrocardiographic signal can also be stably performed.

BRIEF DESCRIPTION OF THE DRAWINGS

The above and other objects, features and advantages of the present disclosure will become more apparent from the following detailed description made with reference to the accompanying drawings. In the drawings:

FIG. 9 is a cross-sectional view illustrating a central cross-section of the electrode potential detection unit together with a user who comes into contact with the seat, as a first modification example of the electrocardiographic waveform measuring apparatus according to the disclosure;

DETAILED DESCRIPTION

A basic principle of an electrocardiographic waveform measuring apparatus according to the disclosure will be described below.

Figure 1:
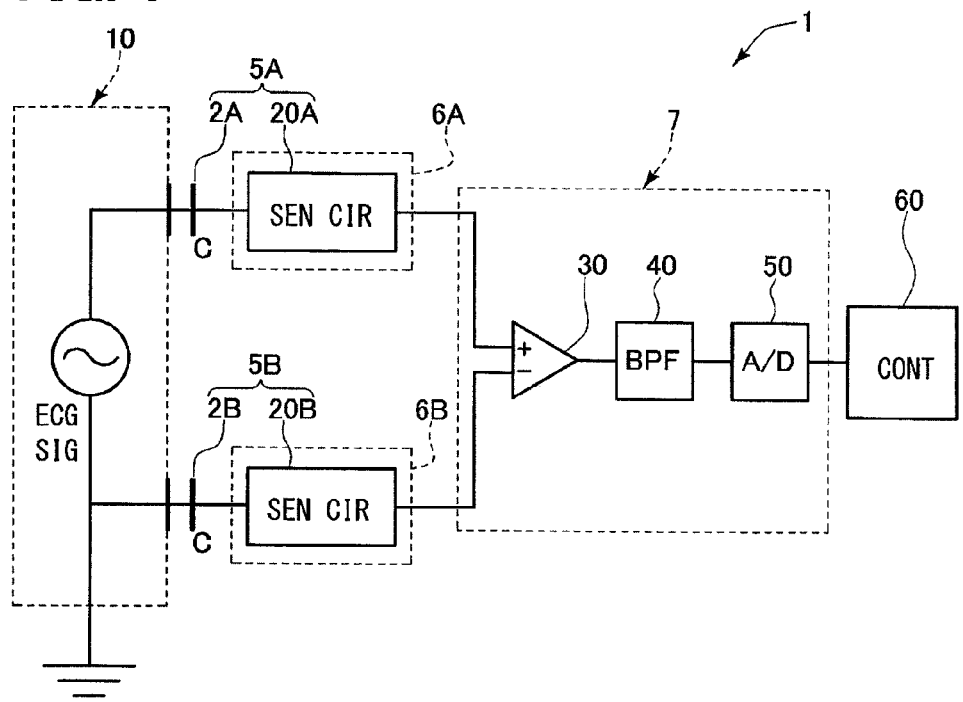
FIG. 1 is a block diagram illustrating an overall configuration of an electrocardiographic waveform measuring apparatus according to the disclosure.

As shown in FIG. 1, an electrocardiographic waveform measuring apparatus 1 according to the present embodiment includes electrode potential detection units 5A and 5B that acquire potentials of paired sensor electrodes 2A and 2B disposed inside a seat 100, respectively, as detection signals, and an electrocardiographic signal extraction unit 7 that generates an electrocardiographic signal in which an electrocardiographic waveform of a user (subject person) 10 who is in contact with the seat 100 is reflected on the basis of each of the detection signals acquired. The electrode potential detection units 5A and 5B include sensor circuits 20A and 20B which are connected to the sensor electrodes 2A and 2B, respectively, and acquire the potentials of the sensor electrodes 2A and 2B to output the acquired potentials as detection signals. The electrocardiographic signal extraction unit 7 includes a differential amplifier circuit 30 that outputs a differential signal obtained by taking a difference between the detection signals which are output from the electrode potential detection units 5A and 5B, and an A/D converter 50 that performs an analog-digital conversion by sampling the differential signal. A digital signal on which the analog-digital conversion is performed is an electrocardiographic signal of the user (subject person) 10 who is in contact with the seat 100, and is input to a control unit (control device) 60.

Figure 2:
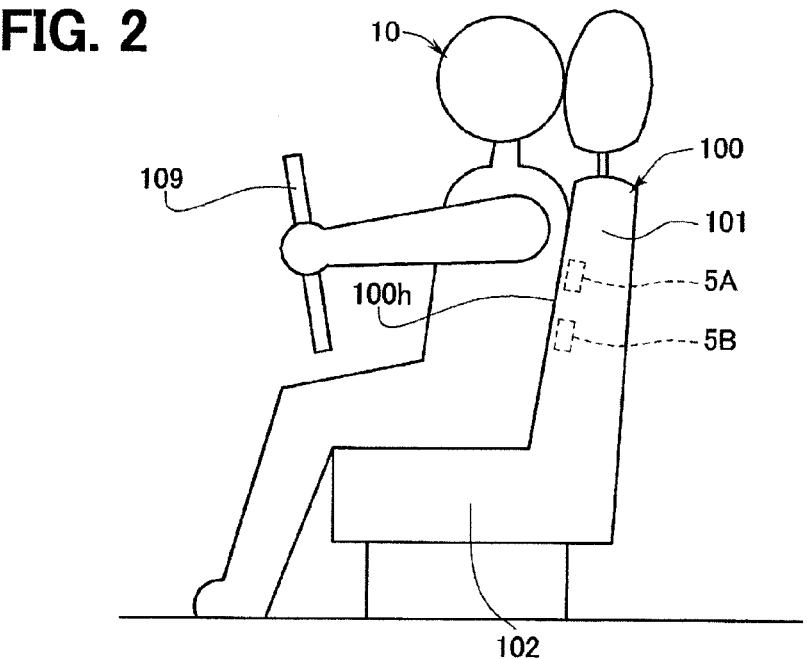
FIG. 2 is a diagram illustrating arrangement positions of electrode potential detection units in a seat provided with the electrocardiographic waveform measuring apparatus according to the disclosure.

As shown in FIG. 2, the paired sensor electrodes 2A and 26 are conductors, and form capacitors C by capacitive coupling between the sensor electrodes and the user 10 who comes into contact with the seat 100. The contact positions of the paired sensor electrodes 2A and 2B with the user 10 are two positions with the heart interposed therebetween in a contact region (for example, back) of the user 10 with the seat 100, and the capacitors C are formed at the two positions, respectively. A weak current flows in a path including the heart of the user 10 (human body) due to a potential difference between the two positions. The weak current indicates a value corresponding to the potential difference between the paired sensor electrodes 2A and 2B, and thus the detection of the potential difference leads to the measurement of the electrocardiographic waveform of the user. A signal obtained by reflecting the potential difference refers to a differential signal which is output from the differential amplifier circuit 30. The control unit 60 receives an input of the signal obtained by reflecting the potential difference, and measures the electrocardiographic waveform of the user on the basis of the signal.

In the present embodiment, the differential signal which is output from the differential amplifier circuit 30 is input to a band-pass filter 40 and is changed to an analog signal obtained by passing through a component of an electrocardiographic signal band (for example, 0.2 Hz to 35 Hz). This analog signal is input to the AD converter 50 and is converted into a digital signal, to obtain an electrocardiographic signal. Meanwhile, the band-pass filter 40 and the AD converter 50 may be omitted.

The features of the electrocardiographic waveform measuring apparatus 1 according to the present embodiment will be described below.

Figure 3:
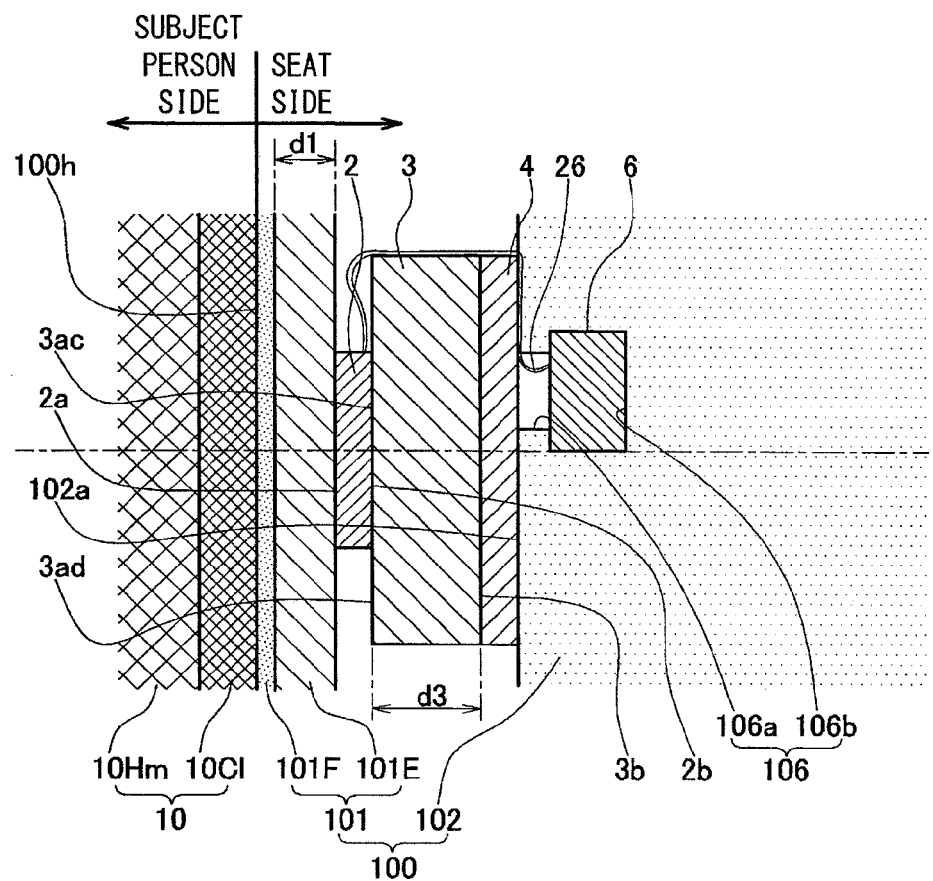
FIG. 3 is a cross-sectional view illustrating a central cross-section of the electrode potential detection unit disposed within the seat together with a user who comes into contact with the seat, in the electrocardiographic waveform measuring apparatus which is an embodiment of the disclosure.

First, the seat 100 provided with the sensor electrodes 2A and 26 will be described. As shown in FIG. 3, the seat 100 is configured such that a seat body covering material 101 that forms a contact surface 100h with the user 10 covers a surface 102a of a seat body material 102 which is separate from the seat body covering material 101. Meanwhile, the seat 100 can be used as a chair, bed or the like, serves as a seat of a vehicle such as an automobile herein, and is used for a user to sit thereon. In addition, the user herein is connected to a GND potential so as to come into contact with an electrode (not shown) connected to a GND terminal (ground terminal) which is provided in a steering wheel 109.

The seat body material 102 is a core material that forms a seating portion 102 and a backrest portion 101 of the seat 100, and is a core material made of, for example, rigid polyurethane foam.

The seat body covering material 101 covers the sensor electrodes 2A and 2B, described above, together with the surface 102a of the seat body material 102 so as to be capable of position displacement relative to the separate seat body material 102. The seat body covering material 101 of the present embodiment is a skin material with an elastic material configured such that an inside elastic material 101E is integrally fixed to the seat interior side of a seat skin material 101F. Herein, the seat skin material 101F and the inside elastic material 101E are fixed to each other by an adhesive, but may be fixed to each other using other fixing methods.

The inside elastic material 101E of the present embodiment is a material having a hardness which is at least equal to or less than that of an insulating material 3 described later, and a thickness d1 thereof is smaller than a thickness d3 of the insulating material 3 described later.

The seat skin material 101F of the present embodiment is made of fabric, leather or the like, and the thickness thereof is equal to or less than 2 mm at a maximum.

Next, the electrode potential detection units 5A and 5B will be described. As shown in FIG. 3, the electrocardiographic waveform measuring apparatus 1 of the present embodiment includes an electrode potential detection unit 5A having the sensor electrode 2A of FIG. 1, and an electrode potential detection unit 5B having the sensor electrode 2B. Meanwhile, the electrode potential detection units 5A and 5B have a common configuration. Therefore, hereinafter, the electrode potential detection units 5A and 5B are represented by sign 5, the sensor electrodes 2A and 2B are represented by sign 2, and the sensor circuits 20A and 20B are represented by sign 20, and then the configurations of both the electrode potential detection units 5 (5A, 5B) will be described.

The electrode potential detection unit 5 includes an electrocardiographic sensor electrode 2 provided inside the seat 100, a guard electrode 4 disposed so as to face the sensor electrode 2 on the opposite side (seat interior side) thereto, the insulating material 3 interposed between the electrode 2 and the electrode 4, a sensor circuit 20 having at least an initial amplifier circuit 20D that amplifies a potential signal which is output from the sensor electrode 2, and a housing case 6 that houses a circuit substrate on which the sensor circuit 20 is formed.

Meanwhile, in the disclosure, the phrase "facing the sensor electrode on the seat interior side (that is, side away from a user who comes into contact with the seat)" as used herein means facing the sensor electrode in a predetermined direction inward of the seat which is toward the inside of the seat from the user contact surface 100h of the seat 100. In addition, the above-mentioned thickness means a width in the direction inward of the seat. For example, the above-mentioned direction inward of the seat can be set to a direction toward the inside of the seat in the piling-up direction of the sensor electrode 2, the insulating material 3 and the guard electrode 4, or a direction toward the inside of the seat which is perpendicular to the user contact surface 100h of the seat 100. Herein, both these directions are coincident with each other, and the coincident direction is set to the above-mentioned direction inward of the seat. Meanwhile, a direction different from this direction may be set to the above-mentioned direction inward of the seat.

As shown in FIG. 2, the sensor electrode 2 is the paired electrodes 2A and 2B which are disposed (herein, interposed vertically therebetween) in the backrest portion 101 of the seat 100 on which the user 10 sits with the average heart position of the user 10 interposed therebetween. The sensor electrode 2 is provided in order to detect a potential generated when the user 10 (human body 10Hm) is brought into contact therewith through clothes 100, the seat body covering material 101, and the like. The sensor electrode 2 is formed of a plate-like conductor (conductor plate) made of a metal material such as, for example, copper, a flexible cloth-like conductor (conductor cloth) having conductivity, a conductor (conductor layer) formed on the insulating material 3, described later, by printing, or the like. The sensor electrode 2 of the present embodiment is a flexible conductor. For example, the above-mentioned cloth-like conductor is assumed to be adopted as the sensor electrode.

The sensor electrode 2 of the present embodiment is disposed on the seat interior side serving as the back side of the user contact surface 100h of the seat body covering material 101. In addition, the sensor electrode 2 of the present embodiment is installed to the seat body material 102 in a state where an electrode surface 2a is exposed so as to be flush with the surface 102a of the seat body material 102 or protrude from the surface 102a, and is configured such that the electrode surface 2a is covered with the seat body covering material 101.

The insulating material (intermediate material) 3 is disposed so as to face the sensor electrode 2 on the opposite side (seat interior side) to the seat body covering material 101. The insulating material 3 covers a rear surface 2b of the sensor electrode 2 opposite to the electrode surface 2a. The insulating material 3 of the present embodiment is disposed so as to be in surface contact with the entire rear surface 2b in a central region 3ac excluding an outer circumferential region 3ad in surfaces 3ac and 3ad on the sensor electrode 2 side. Meanwhile, the insulating material 3 may be disposed in contact with the entire surfaces 3ac and 3ad on the sensor electrode 2 side.

The insulating material 3 is an insulating elastic material having a hardness lower than those of the seat body material 102 and the housing case 6. The hardness of the insulating material 3 has a value within a range of at least equal to or greater than 0.5 N and less than 400 N, more preferably less than 200 N, and still more preferably less than 120 N. The insulating material 3 and the inside elastic material 101E of the present embodiment are flexible polyurethane foam for withstanding load, and are well-known flexible urethane foam (hereinafter, referred to as the elastic material U), containing polyol and polyisocyanate as main components, which is a foamed plastic body formed by performing foaming during resinification. The thickness d3 thereof is 10 mm. The flexible urethane foam is generally a light foamed plastic body having an expansion ratio of appropriately 60 to 10 times and an apparent density of appropriately 16 to 100 kg/m$^3$, which is soft due to air bubbles diffused therethrough and has restorability.

Meanwhile, the hardness of each material has a value which is measured using a measurement method according to each material. The hardness of the flexible urethane foam such as the inside elastic material 101E or the insulating material 3 herein is a hardness which is measured according to a measurement method specified in JIS K6401. The hardness of the inside elastic material 101E or the insulating material 3 in the present embodiment can also be set to be equal to or greater than class X which is specified by, for example, JIS K6401.

The guard electrode 4 is disposed so as to guard against the mixing of noise from the outside into the sensor electrode 2, herein, so as to face the insulating material 3 which is at least an elastic body on the opposite side (seat interior side) to the sensor electrode 2. The guard electrode 4 is located facing the rear surface 2b of the sensor electrode 2 opposite to the electrode surface 2a at the inside of the seat so as to cover the rear surface with the seat interior side. The guard electrode 4 herein is disposed in surface contact with a rear surface 3b (herein, the entirety of a rear surface 3b) of the insulating material 3 so as to cover the rear surface 3b, forming a surface of the insulating material 3 on the inside of the seat, with the inside of the seat.

The guard electrode 4 is formed of a plate-like conductor (conductor plate) made of a metal material such as, for example, copper, a flexible cloth-like conductor (conductor cloth) having conductivity, a conductor (conductor layer) formed on the insulating material 3, described later, by printing, or the like. The guard electrode 4 of the present embodiment is a flexible conductor. For example, the above-mentioned cloth-like conductor is assumed to be adopted as the guard electrode, but other conductors may be used.

Figure 4:
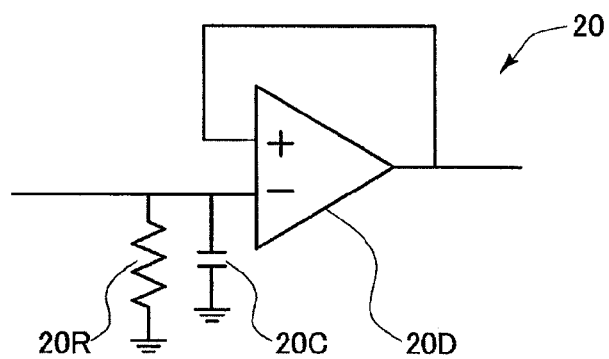
FIG. 4 is a circuit diagram illustrating an example of a circuit configuration of a sensor circuit capable of being adopted in the electrocardiographic waveform measuring apparatus of FIG. 1.

The sensor circuit 20 is a circuit connected to the corresponding sensor electrode 2, and is formed on a circuit substrate (not shown) which is housed in the housing case 6. The sensor circuit 20 includes at least the initial operational amplifier (amplifier circuit) 20D to which a potential signal output from the connecting sensor electrode 2 is input. The operational amplifier 20D of the present embodiment is well-known, and is a circuit of which the output is directly connected to an inverting input terminal (−), for example, as shown in FIG. 4. The operational amplifier is configured such that the sensor electrode 2 is connected to a non-inverting input terminal (+), and the differential amplifier circuit 30 is connected to an output terminal. In addition, the non-inverting input terminal (+) of the operational amplifier 20D is connected to a GND potential (ground potential) through a known resistor 20R, and is connected to a GND potential through a known capacitor 20C.

Meanwhile, the circuit configuration of the sensor circuit 20 is not required to be limited to the configuration of the present embodiment, but may be a configuration of a signal generation circuit, having at least one or more operational amplifiers (amplifier circuits) 20D, which generates and outputs a signal such as to output a signal which is input to the differential amplifier circuit 30 described later and has an electrocardiographic waveform reflected therein, as an output signal. For example, a circuit configuration may be used in which the output of the operational amplifier 20D is input to a correction circuit, and the corrected output is input to the differential amplifier circuit 30. Meanwhile, the output of the sensor circuit 20 may be output to the control unit 60, as it is, to detect an electrocardiographic signal, without using the differential amplifier circuit.

The housing case 6 is cases 6A and 6B harder than the insulating material 3, provided corresponding to the sensor circuits 20A and 20B, respectively, which house circuit substrates 26A and 26B having these circuits 20A and 20B formed thereon. The housing case 6 is a case made of a metal harder than the insulating material 3 or made of a resin, and the thickness thereof is approximately equal to or greater than 2 mm and equal to or less than 5 mm. The housing case 6 is disposed so as to face the insulating material 3 on the opposite side (seat interior side) to the sensor electrode 2.

Meanwhile, the housing case 6 may be disposed facing at least the insulating material 3 at the seat interior side. The housing case 6 of the present embodiment is disposed so as to face the insulating material 3 at the seat interior side, and the insulating material 3 is a thick elastic body. Therefore, when a user brings his/her back into contact with the seat 100 in a state of sitting on the seat, and presses the seat, the insulating material 3 which is an elastic body absorbs the pressure through compressive elastic deformation, and thus the user 10 is not likely to feel (hardly feels) a sense of contact with the hard housing case 6. In addition, the insulating material 3 which is an elastic body is formed thick and at a hardness (softer) lower than that of synthetic rubber (hereinafter, referred to as an elastic material Z) containing natural rubber having, for example, a hardness of 60 (using a type A durometer method). Therefore, the amount of compression caused by elastic deformation is large, and the pressure applied by a user is absorbed more easily. Further, in the present embodiment, since the guard electrode 4 is present at the seat interior side of the insulating material 3, and the housing case 6 is disposed so as to face the guard electrode 4 at the inside of the seat, a sense of contact with the hard housing case 6 is not more likely to be transmitted to the back of the user 10 who sits on the seat 100.

Regarding the thickness d3 of the insulating material 3, the total thickness conforming to the inside elastic material 101E may be equal to or greater than 5 mm, and more preferably equal to or greater than 10 mm, in order not to feel a sense of contact with the hard housing case 6. As the thickness is larger, an adverse influence on sitting comfort caused by the above sense of contact is reduced. However, since an excessive increase in the thickness is contrary to a demand for a reduction in the size of the entire electrode potential detection unit 5, the thickness is set to be equal to or less than 30 mm at a maximum.

However, when an elastic material having a hardness such as the inside elastic material 101E is disposed on the seat exterior side of the sensor electrode 2 as in the present embodiment, there is a problem in that noise increases due to the presence of the elastic material. On the other hand, the thickness d3 of the insulating material 3 is set to be equal to or greater than 2 mm, and thus noise can be reduced up to a level capable of obtaining an electrocardiographic waveform. From the viewpoint of the noise, the thickness d3 of the insulating material 3 may be more preferably equal to or greater than 2 mm, and be still more preferably equal to or greater than 5 mm.

On the other hand, from the viewpoint of the noise and the viewpoint of the detection sensitivity of an electrocardiographic signal, the inside elastic material 101E is preferably as thin as possible. The inside elastic material 101E herein is the same material as that of the insulating material 3 described later, and the thickness d1 thereof is equal to or greater than 1 mm and equal to or less than 10 mm. However, the thickness may be more preferably equal to or greater than 1 mm and equal to or less than 5 mm, and be still more preferably equal to or greater than 1 mm and equal to or less than 2 mm.

A housing concave portion 106 is formed in the seat body material 102 of the present embodiment, and the housing case 6 is housed therein. On the other hand, the sensor electrode 2, the insulating material 3, and the guard electrode 4 are formed integrally with each other in this order, and are bonded onto the surface 102a of the seat body material 102. Meanwhile, in FIG. 3, the sensor electrode 2, the insulating material 3, and the guard electrode 4 look like having relatively large thicknesses, but this is for the purpose of being simply displayed in order to make each portion easy to see. Such thicknesses are not thicknesses obtained by reflecting a real dimensional ratio of each portion, but are sufficiently smaller than those shown in FIG. 3 in reality. The housing concave portion 106 herein includes a housing portion 106b that houses the housing case 6, and a housing inlet port 106a, having a housing port of the housing case 6 formed thereon, which is formed so that the housing case 6 housed in the housing portion 106b comes into contact with the surface on the outer circumferential side and is prevented from falling out. The sensor electrode 2, the insulating material 3 and the guard electrode 4 which are formed integrally with each other are disposed so as to block the housing inlet port 106a. A wiring member 26 which is drawn from the sensor electrode 2 is disposed so as to go into the housing inlet port 106a through the outer circumferential side of the sensor electrode 2, the insulating material 3 and the guard electrode 4 which are formed integrally with each other, and is connected to a circuit substrate within the housing case 6 housed in the housing portion 106b.

The wiring member 26 is a wiring member obtained by coating the outer circumference of a conducting wire with an insulating material. The wiring member 26 herein is a flexible wiring, and is configured to easily cope with a variation in the thickness d3 of the insulating material 3.

Finally, the electrocardiographic signal extraction unit 7 will be described below. As shown in FIG. 1, the electrocardiographic waveform measuring apparatus 1 of the present embodiment includes the electrocardiographic signal extraction unit having the differential amplifier 30, further includes the band-pass filter 40 and the AD converter 50, and is configured such that a generated electrocardiographic signal is input to the control unit 60.

The differential amplifier circuit 30 is constituted by the known differential amplifier 30, and is configured such that the inverting input terminal (−) thereof is connected to the sensor circuit 20A, the non-inverting input terminal (+) thereof is connected to the sensor circuit 20B, and the output terminal thereof is connected to the band-pass filter 40. The differential amplifier 30 outputs a differential signal, obtained by taking a difference between a signal which is input from the sensor circuit 20A and a signal which is input from the sensor circuit 20B, to the band-pass filter 40.

The band-pass filter 40 is constituted by the known band-pass filter 40, and is configured such that the input terminal thereof is connected to the differential amplifier 30, and the output terminal thereof is connected to the AD converter 50. The band-pass filter 40 causes the differential signal which is input from the differential amplifier 30 to pass through an component of an electrocardiographic signal band (for example, "0.2 to 35 [Hz]), attenuates components of bands other than the above band, and then outputs the resultant to the AD converter 50 as an analog signal.

The AD converter 50 is constituted by the known AD converter 50, and is configured such that the input terminal thereof is connected to the band-pass filter 40. The AD converter 50 converts the analog signal which is input from the band-pass filter 40 into a digital signal, and outputs the converted signal as an electrocardiographic signal.

The control unit 60 is a known computer configured to have a known CPU, which includes a storage unit such as a flash memory, and realizes various functions by the CPU executing a program stored in the storage unit. When the input of the electrocardiographic signal is received from the electrocardiographic signal extraction unit 7, the control unit 60 acquires an electrocardiographic waveform on the basis of the electrocardiographic signal. Various processes which are set in advance are then executed on the basis of the acquired electrocardiographic waveform.

In this manner, in the electrocardiographic waveform measuring apparatus 1 of the present embodiment, the sensor electrode 2 is provided immediately below the seat body covering material 101, and the distance of the seat 100 from the contact surface 100h is close, thereby allowing detection sensitivity to be enhanced more than ever before. However, since the disposition of the sensor electrode 2 at a position close to the contact surface 100h of the seat 100 leads to the disposition of the housing case 6 having the sensor circuit 20 at a position close to the contact surface 100h, a problem occurs in that the user 10 who sits on the seat 100 feels a hard housing case in his/her back, and experiences a sense of discomfort. On the other hand, in the electrocardiographic waveform measuring apparatus 1 of the present embodiment, the insulating material 3 which is an elastic member is interposed between the sensor electrode 2 and the guard electrode 4, and thus it is possible to eliminate a sense of touch of a hard housing case which the user 10 who sits on the seat 100 is felt in his/her back. Additionally, the insulating material 3 is thick, and thus it is also possible to obtain a new effect of capable of reducing noise of the detected electrocardiographic signal.

Here, an example of an electrocardiographic waveform acquired and measured in the control unit 60 in reality will be described.

First, in order to increase the detection sensitivity of a signal of the sensor electrode 2, the seat body covering material 101 is taken off so that the sensor electrode 2 is located at a position closer to the user 10, and the sensor electrode is disposed so as to be located immediately below the clothes 10Cl of the user 10 (human body 10Hm). Meanwhile, the insulating material 3 is disposed immediately below the sensor electrode 2, but the insulating material 3 is made of the elastic material Z (herein, seat made of the above-mentioned synthetic rubber) having a thickness of 1 mm. Measurement results of the electrocardiographic waveform in that case is shown in the test A1 of FIG. 5A. Measurement results are obtained in which the electrocardiographic waveform can be sufficiently confirmed in a case of stop of a vehicle, but the electrocardiographic waveform can hardly be detected due to the superimposition of traveling noise in a case of traveling of a vehicle. On the other hand, a problem also remains in that the user who is a subject person feels contact with the hard housing case 6 in his/her back.

Here, FIGS. 5A to 5D are diagrams illustrating an example (test A1) of an electrocardiographic waveform detected in a case where, in the configuration of the electrocardiographic waveform measuring apparatus of FIG. 3, a sensor electrode is disposed immediately below human body clothes, and a change is made so that an insulating material (elastic material Z having a thickness of 1 mm) is disposed between the sensor electrode and a guard electrode, an example (test A2) of an electrocardiographic waveform detected in a case where, in the configuration of the electrocardiographic waveform measuring apparatus of FIG. 3, an inside elastic material (elastic material U having a thickness of 5 mm) is disposed immediately below a seat skin material, the sensor electrode is disposed immediately below the inside elastic material, and a change is made so that an elastic material (elastic material Z having a thickness of 1 mm) is disposed immediately below the sensor electrode, an example (test A3) of an electrocardiographic waveform detected in a case where, in the configuration of the electrocardiographic waveform measuring apparatus of FIG. 3, a change is made so that the sensor electrode is disposed immediately below the human body clothes, and an insulating material (elastic material U having a thickness of 10 mm) is disposed between the sensor electrode and the guard electrode, an example (test A4) of an electrocardiographic waveform detected in a case where, in the same configuration as that of the electrocardiographic waveform measuring apparatus of FIG. 3, an inside elastic material (insulating material U having a thickness of 5 mm) is disposed immediately below the seat skin material, the sensor electrode is disposed immediately below the inside elastic material, and an elastic material (insulating material U having a thickness of 10 mm) is disposed between the sensor electrode and the guard electrode. At test A1, when covering material is taken off from seat body, a sensor electrode is disposed so as to be located immediately below human body clothes, and insulating material located immediately below a sensor electrode is made of elastic material Z having a thickness of 1 mm. At test A1, a measurement can hardly be made during travelling. At test A2, when a seat body is covered with a covering material obtained by bonding an elastic material (i.e., an elastic material U having a thickness of 5 mm) to a rear of a skin material, a sensor electrode is then disposed immediately below an elastic material, and an insulating material located immediately below a sensor electrode is made of an elastic material having a thickness of 1 mm. At test A2, a measurement can hardly be made both during traveling and during stop. At test A3, when a covering material is taken off from a seat body, a sensor electrode is disposed so as to be located immediately below human body clothes, and insulating material located immediately below a sensor electrode is made of elastic material U having a thickness of 10 mm. At test A3, a noise is reduced and measurement can be made. At test A4, when an elastic material (i.e., an insulating material U having a thickness of 5 mm) is disposed immediately below a skin material (i.e., fabric), an electrode is disposed immediately below an elastic material, and an elastic material (i.e., an insulating material U having a thickness of 10 mm) is disposed immediately below an electrode. At test A4, a noise is reduced and a measurement can be made.

Meanwhile, in respective electrocardiographic waveforms shown in the tests A1 to A4 of FIGS. 5A to 5D, places in which the electrocardiographic waveform is saturated are generated due to a signal being saturated by the detachment of a hand from a GND electrode installed to steering. The saturation of the signal is a waveform state capable of being detected even in a normal state, and thus is not equivalent to traveling noise or the like which is desired to be reduced in the disclosure.

In order to improve the problem of a sense of contact with the hard housing case 6, a material is prepared which is obtained by integrally bonding the inside elastic material 101E (having a thickness of 5 mm) made of the elastic material U (herein, flexible urethane foam mentioned above) to the rear surface of the seat skin material (herein, fabric) 101F, and the sensor electrode 2 is disposed immediately below the inside elastic material 101E. Meanwhile, the insulating material 3 having a thickness of 1 mm which is made of the elastic material Z is disposed immediately below the sensor electrode 2. Measurement results in that case are shown in the test A2 of FIG. 5B. This case results in difficulty in measuring the electrocardiographic waveform due to much noise even during the stop of a vehicle. That is, considering that the seat skin material (herein, fabric) 101F is made of the same material as the clothes, the cause of an increase in noise can be said to be the elastic member 101E interposed between the seat skin material 101F and the sensor electrode 2. Meanwhile, the problem of the sense of contact with the hard housing case 6 is not also sufficiently solved by the thickness of the inside elastic material 101E.

Figure 5A:
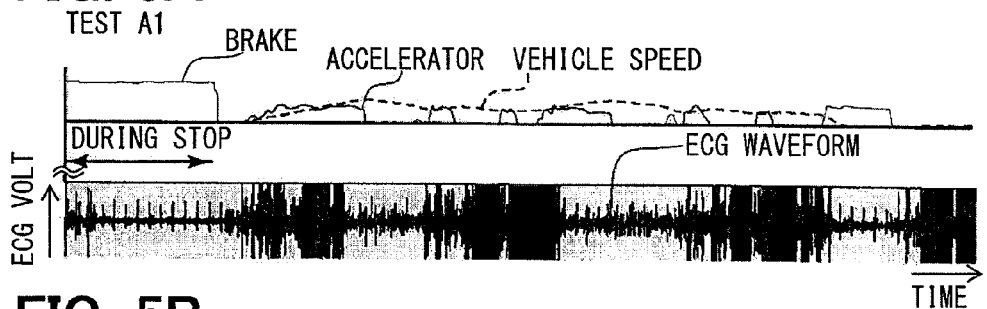
FIGS. 5A to 5D are diagrams illustrating various examples (tests A1 to A4) of an electrocardiographic waveform.

On the other hand, first, in order to solve the problem of the sense of contact with the hard housing case 6, the material of the insulating material 3 is formed of the elastic material U (herein, flexible urethane foam mentioned above) having a lower (softer) hardness from measurement conditions of the test A1 of FIG. 5A, and the thickness thereof is changed to 10 mm. Measurement results in that case are shown in the test A3 of FIG. 5C. It is known that noise is reduced even during traveling a vehicle as compared to the test A1, and that a result of the electrocardiographic waveform being capable of being measured is obtained. In addition, the problem of the sense of contact with the hard housing case 6 is also solved.

Figure 5B:
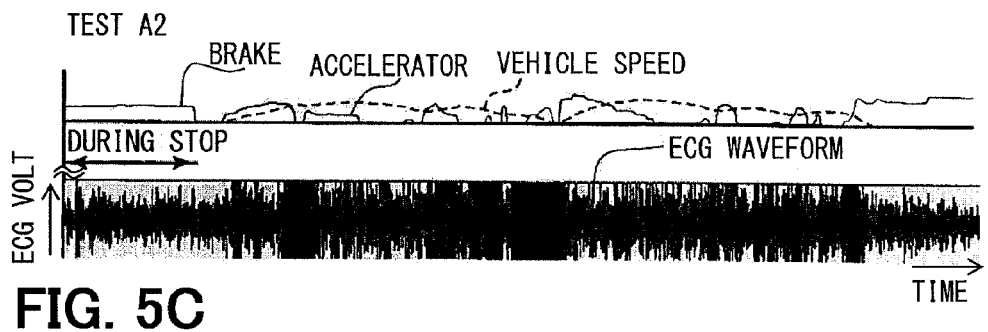
Figure 5C:
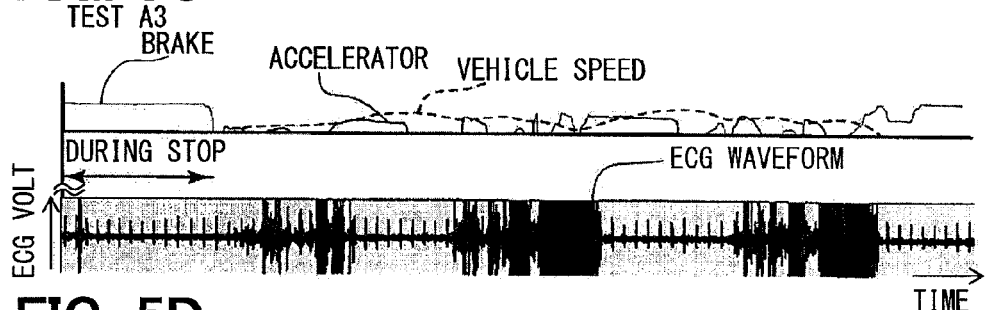
Figure 5D:
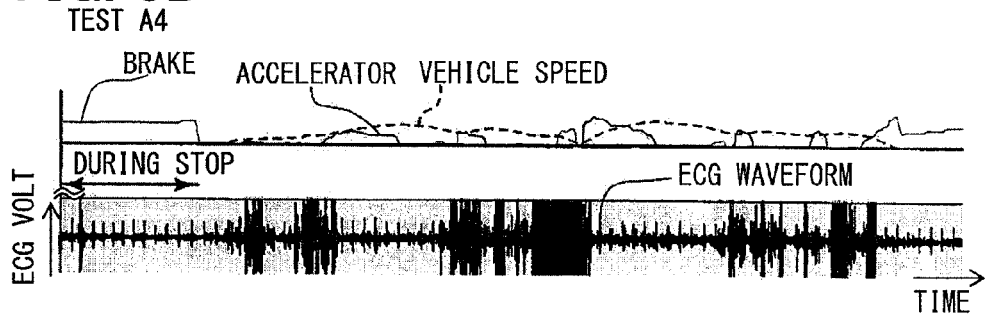

In addition, the material of the insulating material 3 is formed of the elastic material U (herein, flexible urethane foam mentioned above) having a lower (softer) hardness from measurement conditions of the test A2 of FIG. 5B, and the thickness thereof is changed to 10 mm. Measurement results in that case are shown in the test A4 of FIG. 5D. In spite of the elastic member 101E being interposed between the seat skin material (herein, fabric) 101F and the sensor electrode 2, noise during traveling of a vehicle is considerably improved as compared to the test A2 of FIG. 5B, and the electrocardiographic waveform can also be measured during the stop of the vehicle. In addition, the problem of the sense of contact with the hard housing case 6 is also solved.

Figure 6A:
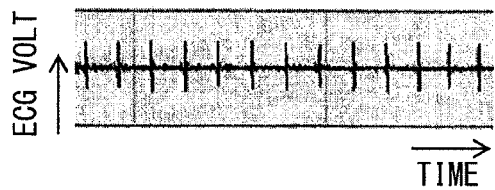
FIGS. 6A to 6J are diagrams illustrating various examples of an electrocardiographic waveform.
Figure 6B:
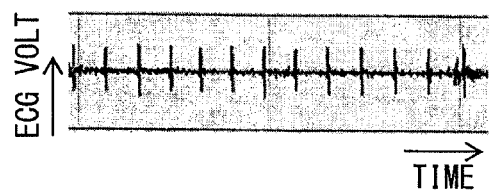

Next, in consideration of the insulating material 3 being used in a compressed state due to pressure caused by the back of the user 10, when the insulating material 3 has a certain amount of thickness in the pressure state, whether noise is reduced up to a level at which the electrocardiographic waveform can be measured is inspected. The results are shown in FIGS. 6A to 6J. A topmost diagram of FIGS. 6A and 6B shows results obtained by measuring the electrocardiographic waveform in the same configuration as that in the test A4 of FIG. 5D. The above-mentioned elastic member U (herein, flexible urethane foam) is adopted as the insulating material 3, and the thickness thereof is set to 10 mm. Based on this, comparisons are made with four measurement results thereunder. Meanwhile, FIGS. 6A to 6J show results obtained by measuring the electrocardiographic waveform two times under each of the conditions. However, on the occasion of the two-time measurements, a user who is a subject person stands up once and sits again on the seat 100.

Figure 6C:
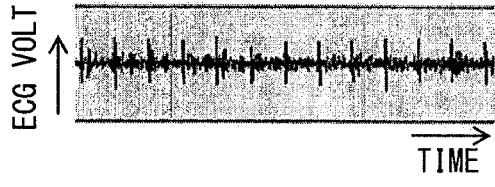
Figure 6D:
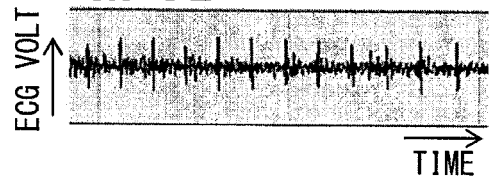
Figure 6E:
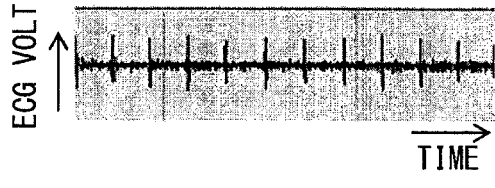
Figure 6F:
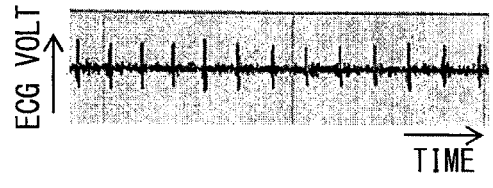
Figure 6G:
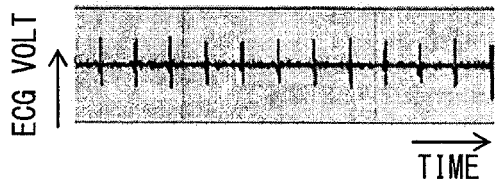
Figure 6H:
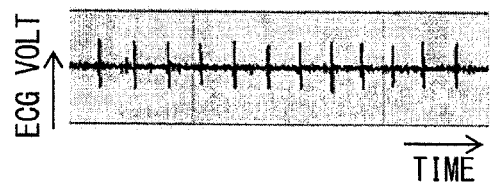
Figure 6I:
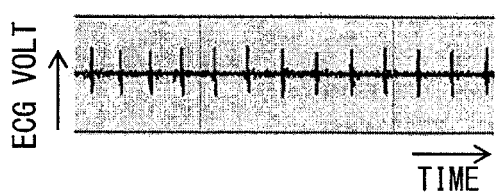
Figure 6J:
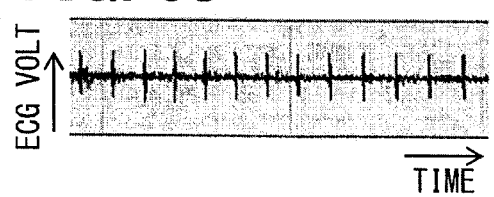

Here, FIGS. 6A to 6J are diagrams illustrating an example of an electrocardiographic waveform detected in a case where, in order to estimate the compressed state of an elastic material during the detection of an electrocardiographic waveform in the electrocardiographic waveform measuring apparatus of FIG. 3 (in which an elastic material having a thickness of 10 mm is disposed as the insulating material U immediately below the sensor electrode), a non-compressed resin plate is disposed instead of the elastic material, and the thickness thereof is changed to 1 mm, 2 mm, 5 mm, and 10 mm. FIG. 6A shows a first measurement of an electrocardiographic (i.e., ECG) waveform in a case where the insulating material is urethane with a thickness of 10 mm, and FIG. 6B shows a second measurement of the ECG waveform in a case where the insulating material is urethane with a thickness of 10 mm. FIG. 6C shows a first measurement of the ECG waveform in a case where the insulating material is a resin plate with a thickness of 1 mm, and FIG. 6D shows a second measurement of the ECG waveform in a case where the insulating material is a resin plate with a thickness of 1 mm. FIG. 6E shows a first measurement of the ECG waveform in a case where the insulating material is a resin plate with a thickness of 2 mm, and FIG. 6F shows a second measurement of the ECG waveform in a case where the insulating material is a resin plate with a thickness of 2 mm. FIG. 6G shows a first measurement of the ECG waveform in a case where the insulating material is a resin plate with a thickness of 5 mm, and FIG. 6H shows a second measurement of the ECG waveform in a case where the insulating material is a resin plate with a thickness of 5 mm. FIG. 6I shows a first measurement of the ECG waveform in a case where the insulating material is a resin plate with a thickness of 10 mm, and FIG. 6J shows a second measurement of the ECG waveform in a case where the insulating material is a resin plate with a thickness of 10 mm.

First, on the assumption that the insulating material 3 is compressed up to a thickness of 1 mm due to pressure caused by the back of a user, a resin plate having a thickness of 1 mm which maintains a non-compression state in the pressure is adopted instead of the insulating material 3. In this case, since noise shows up slightly, the resin plate is not slightly apt for the electrocardiographic waveform (see a second top diagram of FIGS. 6C and 6D). Next, the same resin plate having a thickness of 2 mm is adopted. In this case, noise is found a little, but the resin plate does not a level at which the electrocardiographic waveform can be measured (see a third top diagram of FIGS. 6E and 6F). Next, the same resin plate having a thickness of 5 mm is adopted. In this case, an electrocardiographic waveform signal having the same level as that in the topmost diagram of FIGS. 6A and 6B can be measured (see a fourth top diagram of FIGS. 6G and 6H). Finally, the same resin plate having a thickness of 10 mm is adopted. In this case, an electrocardiographic waveform signal having almost the same level as that in the topmost diagram of FIGS. 6A and 6B can be measured (see a bottommost diagram of FIGS. 6I and 6J).

That is, from the results of FIGS. 6A to 6J, when the insulating material 3 has a thickness equal to or greater than 2 mm, the problem of the sense of contact with the hard housing case 6 can be said to be solved. However, since the compression of the insulating material 3 having a thickness of 2 mm leads to a thickness smaller than 2 mm, it is more preferable that the insulating material have a thickness equal to or greater than 5 mm from the viewpoint of denoising. That is, when the insulating material 3 has a thickness at least equal to or greater than 5 mm, a thickness equal to or greater than 2 mm can be secured even in a case where the insulating material is compressed. Therefore, it is possible to obtain a level (see the third top diagram of FIGS. 6E and 6F) at which the electrocardiographic waveform can be measured.

Next, since the detection sensitivity of an electrocardiographic waveform is different for each user, the noise conditions of the electrocardiographic waveforms between different users, and the influences of the thickness of the insulating material 3 and the change of hardness (1 mm→10 mm and elastic member Z→U) were inspected. The results are shown in FIGS. 7A to 7F. The noise conditions are different from each other due to a difference in each sensitivity in three users A to C who are subject persons. However, when the insulating material 3 is made of the material U and the thickness thereof is changed to 10 mm, noise is reduced with respect to all the three users.

Figure 7A:
FIGS. 7A to 7F are diagrams illustrating an example of electrocardiographic waveforms detected when users are different.
Figure 7B:
Figure 7C:
Figure 7D:
Figure 7E:
Figure 7F:
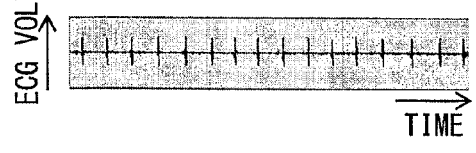

Here, FIGS. 7A to 7F are diagrams illustrating an example of electrocardiographic waveforms detected when users are different, in the electrocardiographic waveform measuring apparatus of FIG. 3 (in which an elastic material having a thickness of 10 mm is disposed as the insulating material U immediately below the sensor electrode), as compared to those when an insulating material is not present immediately below the sensor electrode (instead, a resin plate having a thickness of 1 mm is disposed). Specifically, FIG. 7A is the ECG waveform detected in a case of a subject person A when the insulating material is the resin plate with a thickness of 1 mm, and FIG. 7B is the ECG waveform detected in a case of a subject person A when the insulating material is the resin plate with a thickness of 10 mm. FIG. 7C is the ECG waveform detected in a case of a subject person B when the insulating material is the resin plate with a thickness of 1 mm, and FIG. 7D is the ECG waveform detected in a case of a subject person B when the insulating material is the resin plate with a thickness of 10 mm. FIG. 7E is the ECG waveform detected in a case of a subject person C when the insulating material is the resin plate with a thickness of 1 mm, and FIG. 7F is the ECG waveform detected in a case of a subject person C when the insulating material is the resin plate with a thickness of 10 mm.

Finally, the influence of inner pants worn by a user was inspected. The results are shown in FIGS. 8A to 8D. Regarding inner pants, such as nylon pants for thermal insulation, which are worn so as to adhere relatively closely to a skin, a user who wears the inner pants tends to have more noise than a user who does not wear the inner pants. In the present embodiment, such a tendency was also seen in a case where the above-mentioned resin plate having a thickness of 1 mm is adopted as the insulating material 3. That is, an electrocardiographic waveform (lower left side of FIG. 8C) of the user who wears the inner pants has more noise than an electrocardiographic waveform (upper left side of FIG. 8A) of the user who does not wear the inner pants. However, when the above-mentioned softer elastic material U having a thickness of 10 mm is adopted as the insulating material 3, an electrocardiographic waveform (lower right side of FIG. 8D) when the inner pants are worn also and an electrocardiographic waveform (upper right side of FIG. 8B) when the inner pants are not worn have all less noise.

Figure 8A:
FIGS. 8A to 8D are diagrams illustrating an example of electrocardiographic waveforms detected when a user does not wear inner pants and when the user wears inner pants.
Figure 8B:
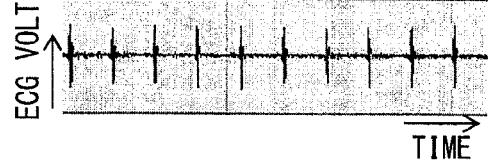
Figure 8C:
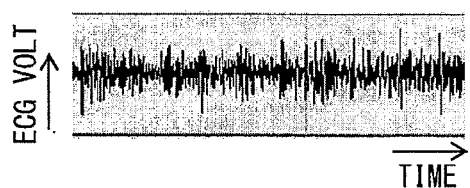
Figure 8D:
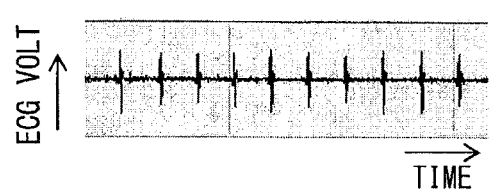

Here, FIGS. 8A to 8D are diagrams illustrating an example of an electrocardiographic waveform detected when a user does not wear inner pants and when the user wears inner pants, in a case where, in the configuration of the electrocardiographic waveform measuring apparatus of FIG. 3, an inside elastic material (elastic material U having a thickness of 5 mm) is disposed immediately below the seat skin material, the sensor electrode is disposed immediately below the inside elastic material, and a change is made so that an insulating material (resin plate having a thickness of 1 mm) is disposed immediately below the sensor electrode, and an example of an electrocardiographic waveform detected when a user does not wear and when the user wears inner pants, in a case where, in the same configuration as that of the electrocardiographic waveform measuring apparatus of FIG. 3, an inside elastic material (insulating material U having a thickness of 5 mm) is disposed immediately below the seat skin material, the sensor electrode is disposed immediately below the inside elastic material, and an insulating material (elastic material U having a thickness of 10 mm) is disposed immediately below the sensor electrode. Specifically, FIG. 8A shows the ECG waveform detected in a case of a subject person D with no inner pants worn when the insulating material is the resin plate with a thickness of 1 mm, and FIG. 8B shows the ECG waveform detected in a case of a subject person D with no inner pants worn when the insulating material is the resin plate with a thickness of 10 mm. FIG. 8C shows the ECG waveform detected in a case of a subject person D with inner pants worn when the insulating material is the resin plate with a thickness of 1 mm, and FIG. 8D shows the ECG waveform detected in a case of a subject person D with inner pants worn when the insulating material is the resin plate with a thickness of 10 mm. As a result, in a case where the inner pants worn, a noise is intense when an elastic material U is not present, but the noise can be removed clearly by inserting an elastic material U.

Meanwhile, noise increasing intervals which are suddenly generated in the electrocardiographic waveforms shown in FIGS. 5A to 8D are generated due to external factors such as a steering operation and a change in a steering grasping position, and are not generated due to the configuration of the electrocardiographic waveform measuring apparatus 1 according to the present embodiment.

It is known through the above-mentioned test results that even when the inside elastic material 101E causing an increase in noise is present, the increased noise can be reduced by making the insulating material 3 which is an elastic member thicker than the seat skin material 101E. In addition, it is known that the noise can be reduced to a level appropriate to electrocardiographic waveform measurement by setting the thickness of the insulating material 3 to be more preferably equal to or greater than 5 mm, and can be reduced to a level appropriate to electrocardiographic waveform measurement by setting the thickness thereof to be still more preferably equal to or greater than 10 mm.

In addition, it is known through the test results that the sitting comfort of the seat 100 having the housing case 6 therein is greatly improved by setting the thickness of the insulating material 3 which is an elastic member to be equal to or greater than 5 mm. In addition, even when the total thickness of the inside elastic material 101E and the insulating material 3 in the configuration of FIG. 3 is set to be equal to or greater than 5 mm, or the thickness of only the insulating material 3 in a case where the inside elastic material 101E is not present is set to be equal to or greater than 5 mm, it is found that the sitting comfort of the seat 100 due to the housing case 6 is greatly improved.

As stated above, although an embodiment of the disclosure has been described herein, the embodiment is merely an example, and the disclosure is not limited thereto. Various changes such as additions and omissions can be made to the embodiment on the basis of the knowledge of those skilled in the art without departing from the scope of the claims appended hereto. Hereinafter, a modification example of the above-mentioned embodiment will be described. Meanwhile, components having functions common to those of the embodiment are denoted by the same reference numerals and signs, and thus the detailed description thereof will not be given. In addition, the above-mentioned embodiment and the following modification example can also be appropriately combined and carried out unless technical contradiction occurs.

In the above-mentioned embodiment, the inside elastic material 101E is integrally fixed onto the opposite side to the contact surface 100h of the seat skin material 101F to form the seat body covering material 101, and the seat body covering material 101 covers the surface 102a of the seat body material 102. The sensor electrode 2 is installed to the seat body material 102 so as to be interposed between the inside elastic material 101E of the seat body covering material 101 and the insulating material 3 on the seat body material 102 side. However, as shown in FIG. 9, the sensor electrode 2 may be installed to the seat body covering material 101 so as to be interposed between a seat skin material 111F and an inside elastic material 111E. In this case, the role of the insulating material 3 constituting an elastic member is played by the inside elastic material 111E. In this case, the inside elastic material 111E is an insulating material constituting an elastic body made of the same material as the insulating material 3 of the above-mentioned embodiment, and a thickness d1' thereof can also be set to be the same as the thickness d3 of the embodiment. Thereby, an electrocardiographic signal having the same level as that in the embodiment can be obtained. According to such a configuration, the sensor electrode 2 and the contact surface 100h of the seat 100 become close to each other, and thus detection sensitivity of the sensor electrode 2 can be increased.

Figure 10:
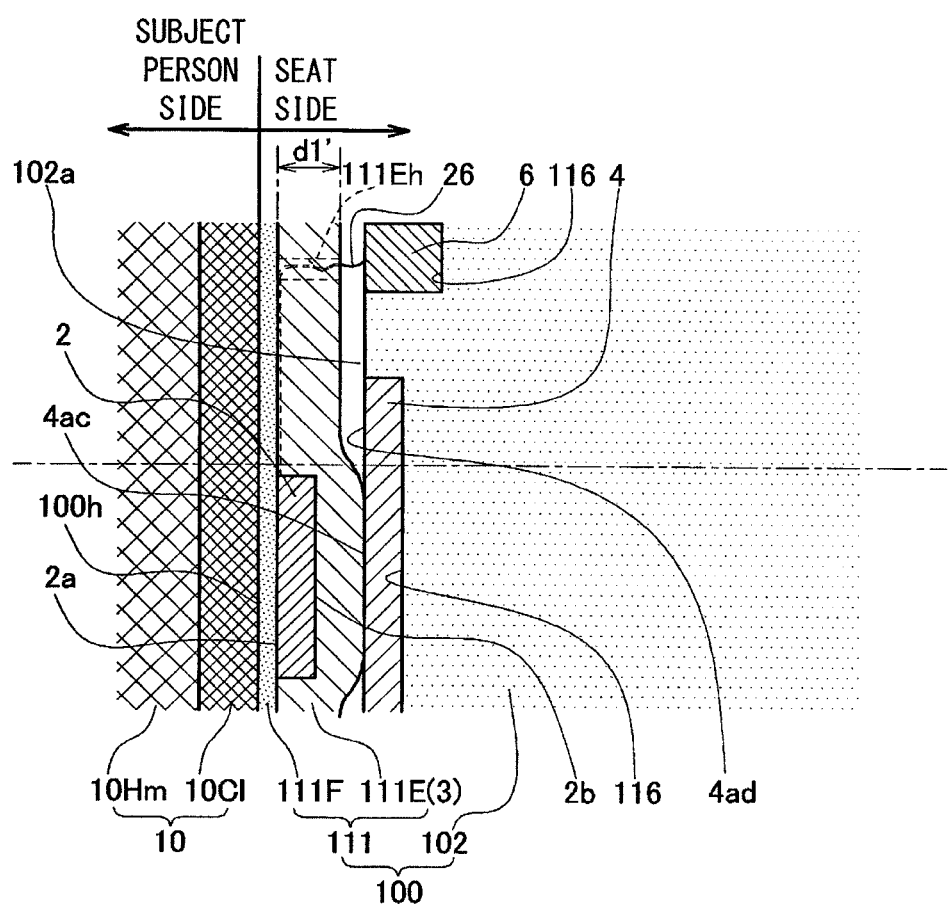
FIG. 10 is a cross-sectional view illustrating a central cross-section of the electrode potential detection unit together with a user who comes into contact with the seat, as a second modification example of the electrocardiographic waveform measuring apparatus according to the disclosure.

In the above-mentioned embodiment, the housing case 6 is disposed facing the seat interior side of the guard electrode 4. However, as shown in FIG. 10, the housing case may be disposed within a seat housing portion 116 serving as the seat interior side of the insulating material 3, on the outer circumferential side of the guard electrode 4.

Figure 11:
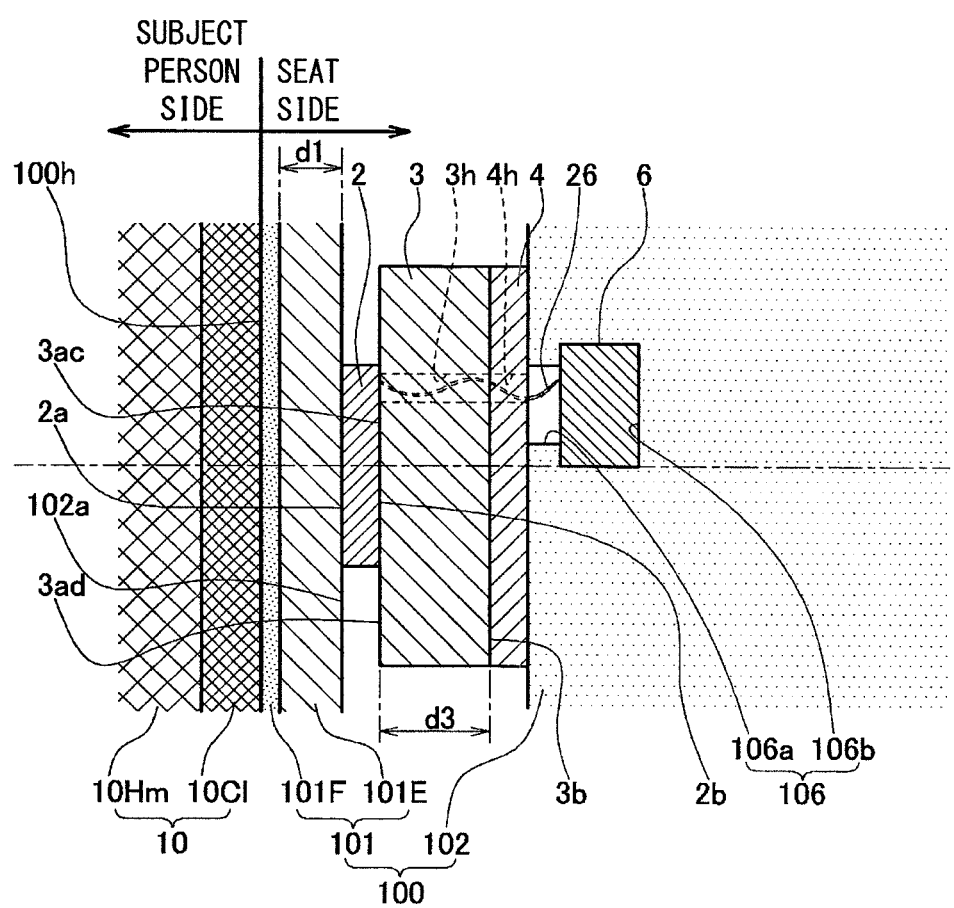
FIG. 11 is a cross-sectional view illustrating a central cross-section of the electrode potential detection unit together with a user who comes into contact with the seat, as a third modification example of the electrocardiographic waveform measuring apparatus according to the disclosure.

In the above-mentioned embodiment, the wiring member 26 is disposed into the housing case 6 so as to wrap around the outer circumferential sides of the sensor electrode 2, the insulating material 3 and the guard electrode 4. However, as shown in FIG. 11, in a state where the insulating material 3 and the guard electrode 4 are provided with wiring passing portions 3h and 4h such as a through hole or a through groove, the wiring member may be disposed so as to pass through the wiring passing portions 3h and 4h.

Figure 12:
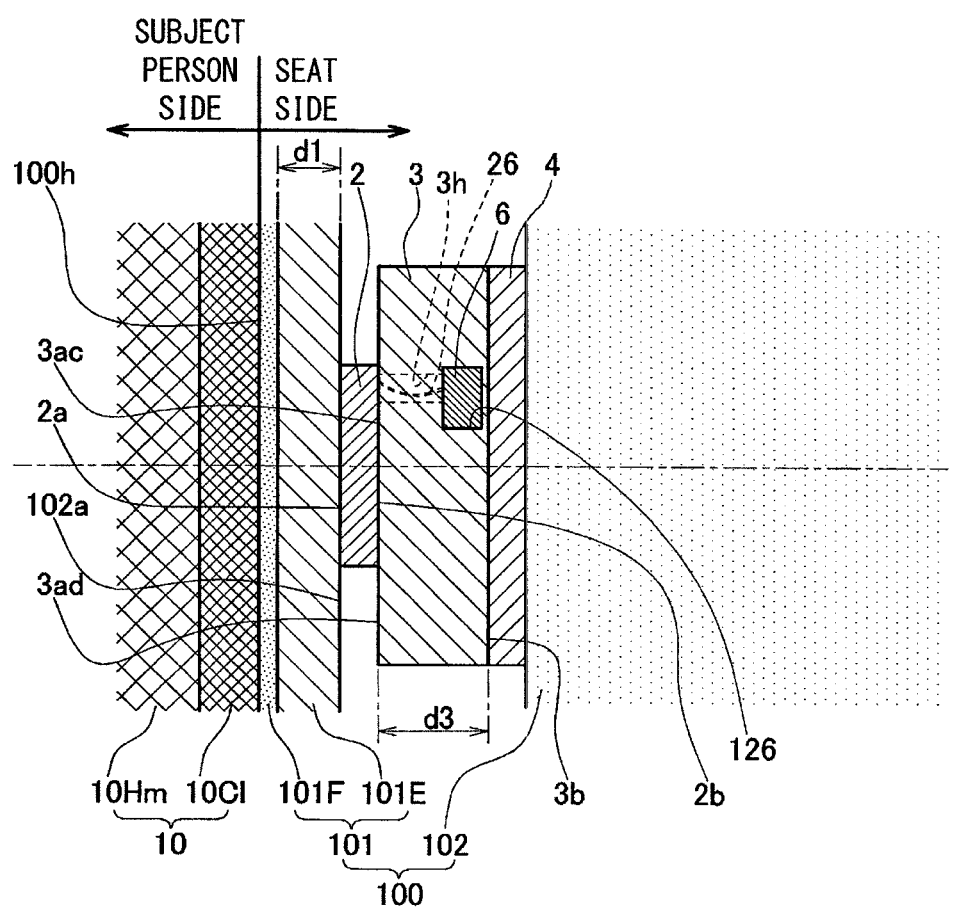
FIG. 12 is a cross-sectional view illustrating a central cross-section of the electrode potential detection unit together with a user who comes into contact with the seat, as a fourth modification example of the electrocardiographic waveform measuring apparatus according to the disclosure.

In the above-mentioned embodiment, the housing case 6 is housed within the seat body material 102, but may be disposed so as to face at least a portion of the insulating material 3 on the seat interior side. For example, as shown in FIG. 12, the housing case 6 may be disposed between the sensor electrode 2 and the guard electrode 4. In this case, the disposition of the housing case 6 close to the guard electrode 4 side can cause the amount of compression based on the elastic deformation of the insulating material 3 to be substantially secured, and thus pressure caused by a user can be sufficiently absorbed. In a case of FIG. 12, an internal space 126 is formed at a position biased to the guard electrode 4 side within the insulating material 3, and the housing case 6 is disposed in the internal space 126.

Second Embodiment

The features of the electrocardiographic waveform measuring apparatus 1 according to the present embodiment will be described below.

Figure 13:
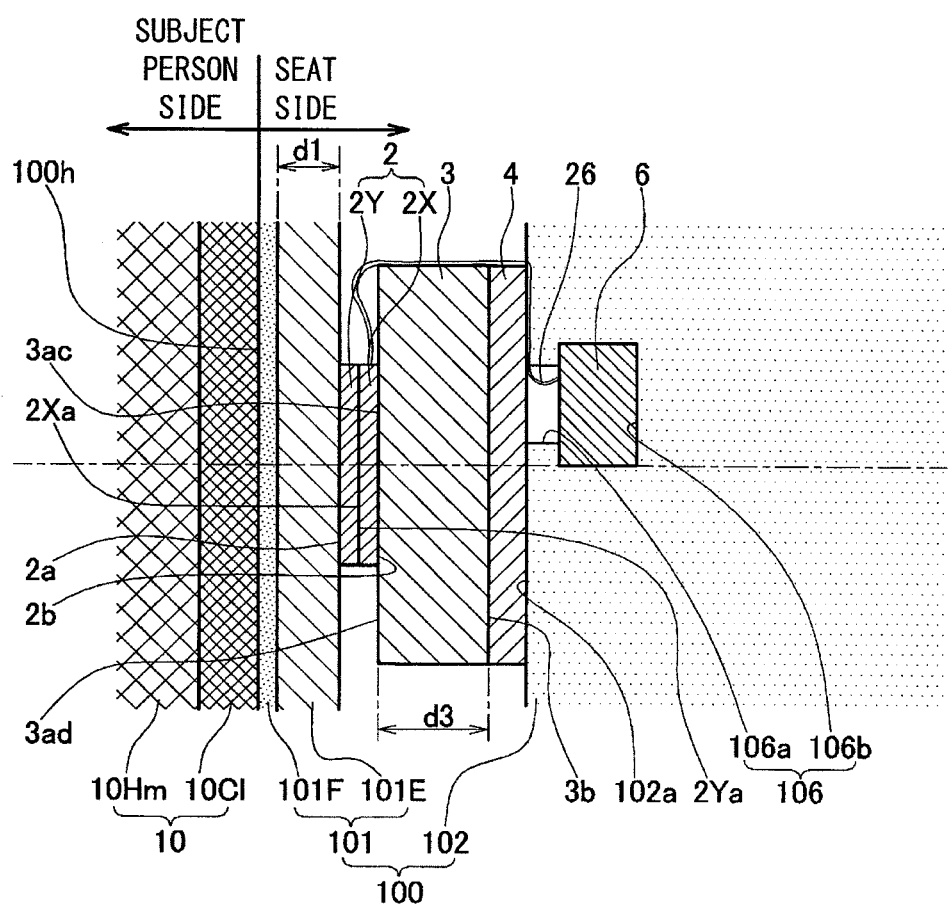
FIG. 13 is a cross-sectional view illustrating a central cross-section of the electrode potential detection unit disposed within the seat together with a user who comes into contact with the seat, in the electrocardiographic waveform measuring apparatus which is a second embodiment of the disclosure.

First, the seat 100 provided with the sensor electrodes 2A and 2B will be described. As shown in FIG. 13, the seat 100 is configured such that a seat body covering material 101 that forms a contact surface 100h with the user 10 covers a surface 102a of a seat body material 102 which is separate from the seat body covering material 101. Meanwhile, the seat 100 can be used as a chair, bed or the like, serves as a seat of a vehicle such as an automobile herein, and is used for a user to sit thereon. In addition, the user herein is connected to a GND potential so as to come into contact with an electrode (not shown) connected to a GND terminal (ground terminal) which is provided in a steering wheel 109.

The seat body material 102 is a core material that forms a seating portion 100A and a backrest portion 100B of the seat 100, and is a core material made of, for example, rigid polyurethane foam.

The sensor electrode 2 of the present embodiment is disposed on the seat interior side serving as the back side of the user contact surface 100h of the seat body covering material 101. In addition, the sensor electrode 2 of the present embodiment is installed to the seat body material 102 in a state where an electrode surface 2a is exposed so as to be flush with the surface 102a of the seat body material 102 or protrude from the surface 102a, and is configured such that the electrode surface 2a is covered with the seat body covering material 101.

The sensor electrode 2 of the present embodiment are constituted by a first sensor electrode 2X and a second sensor electrode 2Y which are separate from each other. The first sensor electrode 2X has a first electrode surface 2Xa which is installed on the seat body material 102 and is exposed to the seat body covering material 101 side. The second sensor electrode 2Y has a second electrode surface 2Ya which is installed on the seat body covering material 101 and slidably comes into contact with the first electrode surface 2Xa. That is, the second sensor electrode 2Y slides on the electrode surface 2Xa of the first sensor electrode 2X in accordance with the sliding or the like of the seat body covering material 101 with respect to the seat body material 102.

The first and second sensor electrodes 2X and 2Y are formed of a plate-like conductor (conductive plate) made of a metal material such as, for example, copper, a flexible cloth-like conductor (conductor cloth) having conductivity, a conductor (conductive layer) formed by printing, or the like.

Both the first and second sensor electrodes 2X and 2Y of the present embodiment are flexible conductors. For example, the above-mentioned cloth-like conductor is assumed to be adopted as the sensor electrodes, but other conductors may be used. The second sensor electrode 2Y herein is fixed to a rear surface serving as the seat interior side of the seat body covering material 101 by bonding, sewing or the like, and the first sensor electrode 2X is fixed to a surface serving as the seat exterior side of the insulating material 3, described above, by bonding, sewing or the like. In addition, the first sensor electrode 2X is installed to the seat body material 102 so as to be flush with the surface 102a or to protrude from the surface 102a to the outside of the seat, and comes into contact with the second sensor electrode 2Y.

The insulating material (intermediate material) 3 is disposed so as to face the first sensor electrode 2X on the opposite side (seat interior side) to the seat body covering material 101. The insulating material 3 covers a rear surface 2b of the first sensor electrode 2X opposite to the electrode surface 2Xa. Specifically, the insulating material 3 of the present embodiment is disposed so as to be in surface contact with the entire rear surface 2b of the first sensor electrode 2X in a central region 3ac excluding an outer circumferential region 3ad in surfaces 3ac and 3ad on the first sensor electrode 2X side. Meanwhile, the insulating material 3 may be disposed in contact with the entire surfaces 3ac and 3ad on the sensor electrode 2 side.

The guard electrode 4 is disposed so as to guard against the mixing of noise from the outside into the sensor electrode 2 (chiefly, first sensor electrode 2X), herein, so as to face the insulating material 3 which is at least an elastic body on the opposite side (seat interior side) to the sensor electrode 2. The guard electrode 4 is located facing the rear surface (herein rear surface of the first sensor electrode 2X) 2b of the sensor electrode 2 opposite to the electrode surface 2a at the inside of the seat so as to cover the rear surface with the seat interior side. The guard electrode 4 herein is disposed in surface contact with a rear surface 3b (herein, the entirety of a rear surface 3b) of the insulating material 3 so as to cover the rear surface 3b, forming a surface of the insulating material 3 on the inside of the seat, with the inside of the seat.

In this manner, in the electrocardiographic waveform measuring apparatus 1 of the present embodiment, there is the possibility of the local generation of discharge to the sensor electrode 2Y on the seat body material 102 side from the seat body covering material 101 which has a tendency to accumulate static charge due to sliding or the like between the seat body material 102 and the seat body covering material 101, when the sensor electrode 2Y is provided immediately below the seat body covering material 101. Therefore, the separate electrode 2X is also provided on the seat body covering material 101 side which has a tendency to accumulate static charge, and the sensor electrode 2 is formed so as to be brought into contact with the electrode 2X and the electrode 2Y. Thereby, since static charge accumulated in the seat body covering material 101 is immediately diffused into the electrode surface 2Ya of the second sensor electrode 2Y on the seat body covering material 101 side, local discharge does not occur.

Here, the electrocardiographic waveform acquired and measured in the control unit 60 in reality will be described.

Figure 14A:
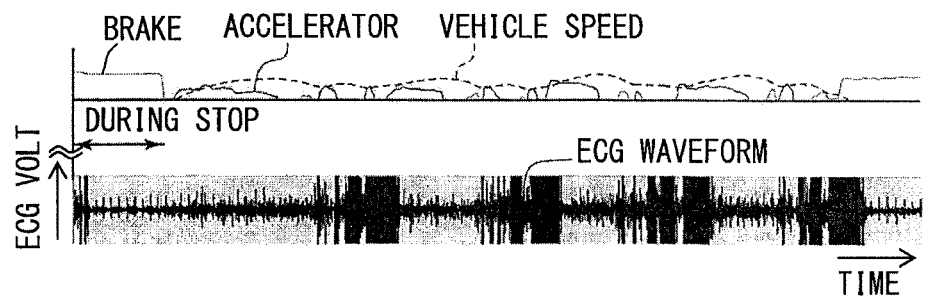
FIGS. 14A and 14B are diagrams illustrating a comparison of an electrocardiographic waveform detected in the electrocardiographic waveform measuring apparatus of FIG. 13 with an electrocardiographic waveform detected when sensor electrodes are changed to one non-separated electrode in the electrocardiographic waveform measuring apparatus of FIG. 13.
Figure 14B:
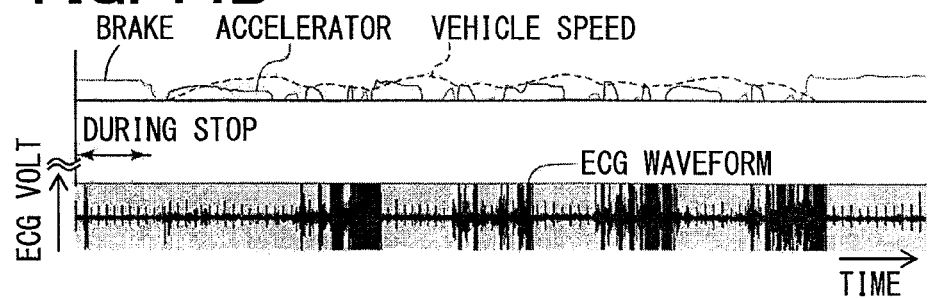

An upper diagram of FIG. 14A shows an electrocardiographic waveform when the electrode 2Y is excluded from the configuration of the present embodiment (with electrode separation), and a lower diagram of FIG. 14B shows an electrocardiographic waveform when both the electrode 2X and the electrode 2Y are provided in the configuration of the present embodiment (without electrode separation). Here, FIG. 14A shows a case where an apparatus has no sensor electrode separation, and FIG. 14B shows a case where the apparatus has sensor electrode separation. It is known from FIGS. 14A and 14B that in a case (lower diagram) in which the sensor electrode 2 is separated into the electrode 2X and the electrode 2Y, one electrode 2Y is fixed to the seat body covering material 101, the other electrode 2X is fixed to the seat body 102, and both these electrodes 2Y and 2X are disposed so as to come into contact with each other and slide with respect to each other, baseline noise can be reduced more considerably than in a case where one sensor electrode 2 is provided without being separated into the electrode 2X and the electrode 2Y, and is fixed to the seat body 102.

Meanwhile, noise increasing intervals which are suddenly generated in the electrocardiographic waveforms shown in FIG. 14 are generated due to external factors such as a steering operation and a change in a steering grasping position, and are not generated due to the configuration of the electrocardiographic waveform measuring apparatus 1 according to the present embodiment.

However, in the electrocardiographic waveform measuring apparatus 1 of the present embodiment, the sensor electrode 2 is provided immediately below the seat body covering material 101, and the distance of the seat 100 from the contact surface 100h is close, thereby allowing detection sensitivity to be enhanced more than ever before. However, since the disposition of the sensor electrode 2 at a position close to the contact surface 100h of the seat 100 leads to the disposition of the housing case 6 having the sensor circuit 20 at a position close to the contact surface 100h, a problem occurs in that the user 10 who sits on the seat 100 feels a hard housing case in his/her back, and experiences a sense of discomfort. On the other hand, in the electrocardiographic waveform measuring apparatus 1 of the present embodiment, the insulating material 4 which is an elastic member is interposed between the sensor electrode 2 and the guard electrode 4, and thus it is possible to eliminate a sense of touch of a hard housing case which the user 10 who sits on the seat 100 is felt in his/her back. Additionally, the insulating material 3 is thick, and thus it is also possible to obtain a new effect of capable of reducing noise of the detected electrocardiographic signal.

Specifically, it is known that through various test results that a problem of the sitting comfort such as a user's feeling of contact with the hard housing case 6 on his/her back is greatly improved by setting the thickness of the insulating material 3 which is an elastic member to be equal to or greater than 5 mm. In addition, even when the total thickness of the inside elastic material 101E and the insulating material 3 in the configuration of FIG. 13 is set to be equal to or greater than 5 mm, or the thickness of only the insulating material 3 in a case where the inside elastic material 101E is not present is set to be equal to or greater than 5 mm, it is found that the sitting comfort of the seat 100 due to the housing case 6 is greatly improved.

In addition, it is known through various test results that even when the inside elastic material 101E causing an increase in noise is present, the increased noise can be reduced by making the insulating material 3 which is an elastic member thicker than the seat skin material 101E. In addition, it is known that the noise can be reduced to a level appropriate to electrocardiographic waveform measurement by setting the thickness of the insulating material 3 to be more preferably equal to or greater than 5 mm, and can be reduced to a level appropriate to electrocardiographic waveform measurement by setting the thickness thereof to be still more preferably equal to or greater than 10 mm.

As stated above, although an embodiment of the disclosure has been described herein, the embodiment is merely an example, and the disclosure is not limited thereto. Various changes such as additions and omissions can be made to the embodiment on the basis of the knowledge of those skilled in the art without departing from the scope of the claims appended hereto.

Figure 15:
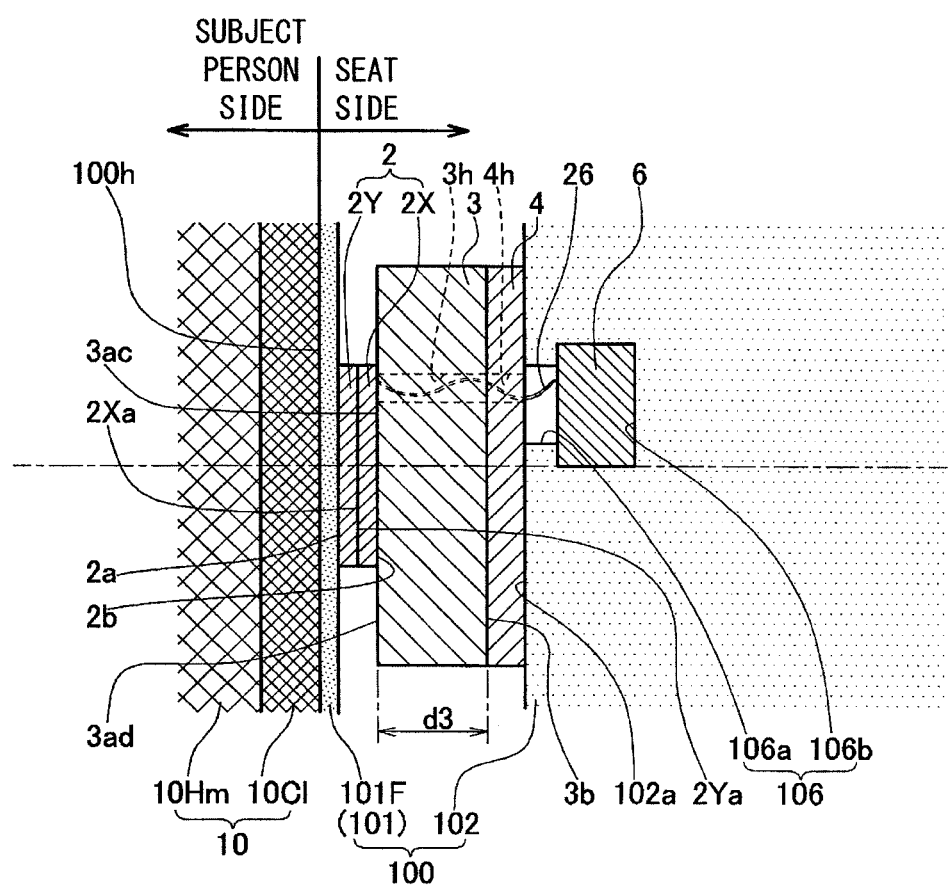
FIG. 15 is a cross-sectional view similar to FIG. 13 illustrating a first modification example of the electrocardiographic waveform measuring apparatus of FIG. 1.

For example, as shown in FIG. 15, a configuration may be adopted in which the inside elastic material 101E is omitted, only the seat skin material 101F is used as the seat body covering material 101, and the electrode 2Y is fixed to the seat skin material 101F. Meanwhile, the seat body covering material 101 may be formed so that two or more materials are fixed thereto.

In the above-mentioned embodiment, the wiring member 26 is disposed into the housing case 6 so as to wrap around the outer circumferential sides of the sensor electrode 2, the insulating material 3 and the guard electrode 4. However, as shown in FIG. 15, in a state where the insulating material 3 and the guard electrode 4 are provided with wiring passing portions 3h and 4h such as a through hole or a through groove, the wiring member may be disposed so as to pass through the wiring passing portions 3h and 4h.

Figure 16:
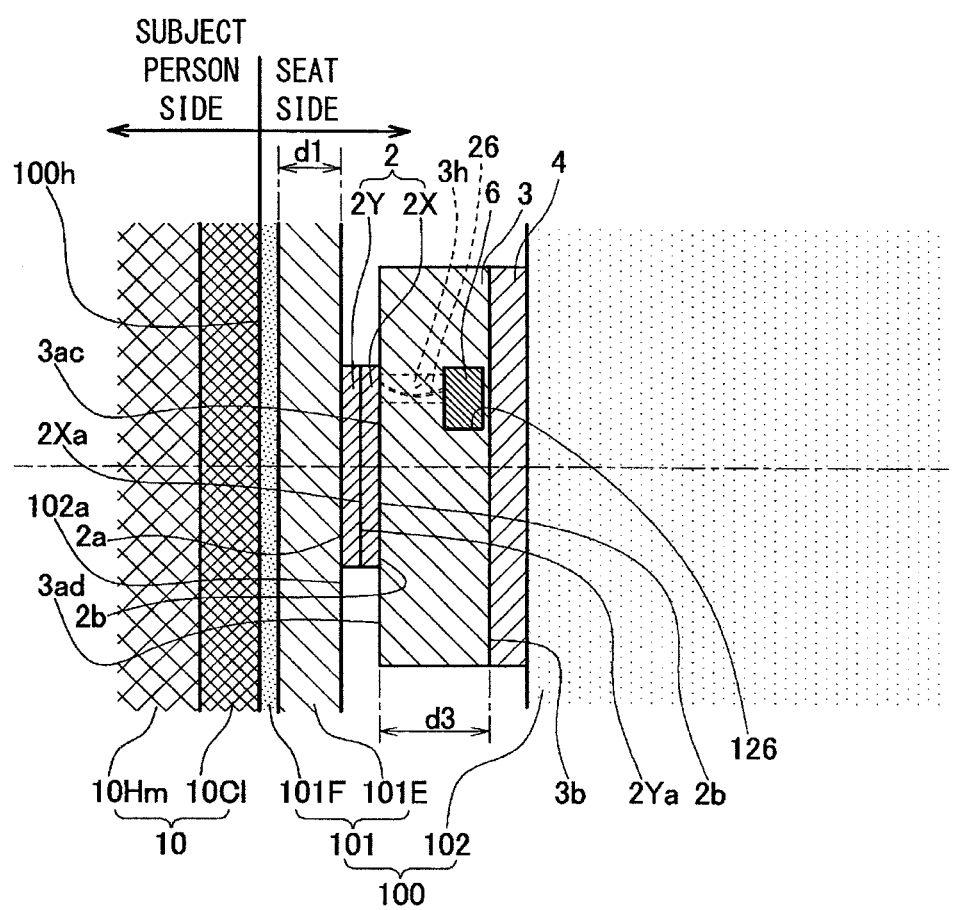
FIG. 16 is a cross-sectional view similar to FIG. 13 illustrating a second modification example of the electrocardiographic waveform measuring apparatus of FIG. 1.

In the above-mentioned embodiment, the housing case 6 is housed within the seat body material 102, but may be disposed so as to face at least a portion of the insulating material 3 on the seat interior side. For example, as shown in FIG. 16, the housing case 6 may be disposed between the sensor electrode 2 and the guard electrode 4. In this case, the disposition of the housing case 6 close to the guard electrode 4 side can cause the amount of compression based on the elastic deformation of the insulating material 3 to be substantially secured, and thus pressure caused by a user can be sufficiently absorbed. In a case of FIG. 16, an internal space 126 is formed at a position biased to the guard electrode 4 side within the insulating material 3, and the housing case 6 is disposed in the internal space 126.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

What is claimed is:

1. An electrocardiographic waveform measuring apparatus mounted in a seat having a seat skin element, which provides a contact surface with a user, the electrocardiographic waveform measuring apparatus comprising:
   a sensor electrode disposed at a seat interior side of the seat as a back side of the contact surface so that the sensor electrode is covered with the seat skin element;
   an insulating elastic element disposed at the seat interior side of the sensor electrode in the seat opposite to the seat skin element so that the insulating elastic element faces the sensor electrode, and the insulating elastic element has a thickness larger than a thickness of the seat skin element;
   a guard electrode disposed at the seat interior side of the insulating elastic element in the seat opposite to the sensor electrode so that the guard electrode is opposed to the sensor electrode through the insulating elastic element; and
   a housing case disposed at the seat interior side of the insulating elastic element in the seat opposite to the sensor electrode so that the housing case is opposite to the insulating elastic element, the housing case accommodating a sensor circuit with at least an amplifier circuit, to which a potential signal indicating a potential of the sensor electrode is initially input.

2. The electrocardiographic waveform measuring apparatus according to claim 1,
   wherein the insulating elastic element has a hardness equal to or greater than 0.5 N and equal to or less than 400 N, and
   wherein the insulating elastic element has a thickness equal to or greater than 2 mm and equal to or less than 30 mm.

3. The electrocardiographic waveform measuring apparatus according to claim 1,
   wherein the housing case is disposed at the seat interior side of the guard electrode in the seat opposite to the insulating elastic element so that the housing case faces the guard electrode.

4. The electrocardiographic waveform measuring apparatus according to claim 1, further comprising:
   an inside elastic element integrally fixed to the seat skin element opposite to the contact surface.

5. The electrocardiographic waveform measuring apparatus according to claim 1,
   wherein the seat further includes a seat body element, which is different from the seat skin element,
   wherein the seat skin element covers a surface of the seat body element,
   wherein the sensor electrode is installed to the seat body element so as to expose an electrode surface of the sensor electrode from the seat body element on a contact surface side, and
   wherein the electrode surface of the sensor electrode is covered with the seat skin element on the contact surface side.

6. The electrocardiographic waveform measuring apparatus according to claim 1,
   wherein the insulating elastic element has a thickness equal to or greater than 5 mm.

7. The electrocardiographic waveform measuring apparatus according to claim 1,
   wherein the sensor electrode is connected to the sensor circuit through a flexible wiring.

* * * * *